(12) United States Patent
Sawaguchi et al.

(10) Patent No.: US 8,461,265 B2
(45) Date of Patent: Jun. 11, 2013

(54) TRIBLOCK COPOLYMER HAVING BIODEGRADABLE POLYMER BLOCKS AND METHOD OF PRODUCING THE SAME

(75) Inventors: Takashi Sawaguchi, Tokyo (JP); Daisuke Sasaki, Saitama (JP)

(73) Assignee: San-Ei Kougyou Corporation, Saitama (JP)

( * ) Notice: Subject to any disclaimer, the term of this patent is extended or adjusted under 35 U.S.C. 154(b) by 0 days.

(21) Appl. No.: 12/919,709

(22) PCT Filed: Feb. 27, 2009

(86) PCT No.: PCT/JP2009/000894
§ 371 (c)(1), (2), (4) Date: Nov. 12, 2010

(87) PCT Pub. No.: WO2009/107396
PCT Pub. Date: Sep. 3, 2009

(65) Prior Publication Data
US 2011/0046308 A1 Feb. 24, 2011

(30) Foreign Application Priority Data
Feb. 29, 2008 (JP) .................. 2008-050601

(51) Int. Cl.
C08G 59/32 (2006.01)

(52) U.S. Cl.
USPC ........... 525/186; 525/410; 525/412; 525/415; 525/450

(58) Field of Classification Search
USPC .................. 525/186, 410, 412, 415, 450
See application file for complete search history.

(56) References Cited

U.S. PATENT DOCUMENTS

| 3,585,257 | A | * | 6/1971 | Mueller et al. ................ | 525/114 |
| 5,449,743 | A | * | 9/1995 | Kobayashi et al. ............ | 528/355 |
| 7,160,949 | B2 | * | 1/2007 | Ota et al. ...................... | 525/242 |

FOREIGN PATENT DOCUMENTS

| JP | 2001-270924 | | 10/2001 |
| JP | 2007-321141 | | 12/2003 |
| JP | 2007-177039 | | 7/2007 |
| JP | 2007-321141 | * | 12/2007 |
| JP | 2008-037996 | * | 2/2008 |
| WO | WO 2005/078017 | | 8/2005 |

OTHER PUBLICATIONS

Han, C.J.; Lee, M.S.; Byun, D.J.; Kim, S.Y.; Macromolecules, 2002, vol. 35, p. 8923-8925.*
Frick, E.M.; Zalusky, A.; Hillmyer, M.A.; Biomacromolecules, 2003, vol. 4, p. 216-223.*
Han, C.J., et al.; Macromolecules, 2002, vol. 35, p. 8923-8925.*
International Search Report from corresponding PCT Application No. PCT/JP2009/000894 dated Apr. 21, 2009.
Sasaki, D., *Synthesis and Applications of Triblock and Multiblock Copolymers Using Telechelic Oligopropylene*, Polymer, 2008, vol. 49 (pp. 4094-4100).
Hagiwara, T., *Functionalization and Applications of Telechelic Oligopropylenes: Preparation of Alpha, omega-Dihydroxy and Diaminooligopropylenes*, Macromolecules, 2005, vol. 38 (pp. 10373-10378).
Nathaniel, A., *Influence of Polydispersity on the Self-Assembly of Diblock Copolymers*, Macromolecules, 2005, vol. 38 (pp. 8803-8810).
Network Polymer, vol. 23, No. 2, 43-51 (2002)—with a partial translation—2 pages.
Kuroki et al, Determination of Chemical Structures by 1H- and 13C-NMR for Thermally Degraded Linear High Density Polyethylene, Journal of Polymer Science: Polymer Chemistry Edition, vol. 21, 703-714 (1983).
Sawaguchi et al., Preparation of a,w- Diisopropenyloligopropylene by Thermal Degradation of Isotactic Polypropylene, Macromolecules, vol. 28, No. 24, 6 pages (Nov. 20, 1995).
Schmidt et al., Synthesis and Characterization of Model Polyisoprene- Polylactide Diblock Copolymers, Macromolecules 1999, 32, 4794-4801.
Wang et al., Synthesis of Polybutadiene- Polylactide Diblock Copolymers Using Aluminum Alkoxide Macroinitiators. Kinetics and Mechanism, Macromolecules 2000, 33, 7395-7403.

* cited by examiner

Primary Examiner — Robert Jones, Jr.
(74) Attorney, Agent, or Firm — Ohlandt, Greeley, Ruggiero & Perle, LLP.

(57) ABSTRACT

This invention provides a triblock copolymer useful as a compatibilizer for biodegradable polymers, such as polylactic acid, and general-purpose polymers.

Namely, this is a triblock copolymer represented by the below general formula (i), wherein each $R^1$ is independently selected from the group consisting of H, $-CH_3$, $-C_2H_5$, and $-CH_2CH(CH_3)_2$, n is an integer of 10 to 1000, and A represents a polyester block obtained by subjecting one or more cyclic esters selected from the group consisting of lactides, glycolides and lactones, to ring-opening polymerization.

[Chemical Formula 1]

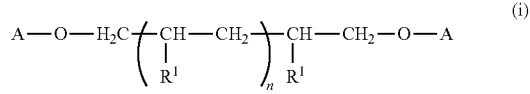

(i)

3 Claims, 2 Drawing Sheets

¹H NMR spectrum of iPP-OH

¹H NMR spectrum of PLA-iPP-PLA triblock copolymer.

1H NMR spectrum of PCL-iPP-PCL triblock copolymer.

TRIBLOCK COPOLYMER HAVING BIODEGRADABLE POLYMER BLOCKS AND METHOD OF PRODUCING THE SAME

TECHNICAL FIELD

The present invention relates to a triblock copolymer having a novel structure and to a method of producing the same.

BACKGROUND ART

Recently, from the viewpoint of conservation of the environment, various biodegradable polymers which can be decomposed in the natural environment due to the working of microorganisms present in soil or water have been developed. Among these biodegradable polymers, examples of known biodegradable polymers that can be melt-formed include: polyhydroxybutyrate; polycaprolactone; and aliphatic polyesters and polylactic acids composed of an aliphatic dicarboxylic acid component, such as succinic acid or adipic acid, and a glycol component, such as ethylene glycol or butanediol.

Among them, polylactic acid-based biodegradable polymers have excellent characteristics such as high heat resistance and high strength compared to other biodegradable polymers. Polycaprolactone-based biodegradable polymers have the characteristic that they can be molded and processed into films or plastic fibers by injection molding, extrusion molding, or melt spinning. However, these biodegradable polymers have drawbacks, for example, in shock resistance, flexibility, and rapid reduction in properties during biodegradation, and their applicable use is limited.

Therefore, attempts at blending a plurality of biodegradable polymers have been made. For example, as shown in Patent Document 1 and Patent Document 2, attempts at blending polylactic acid with various polymers have been made in order to improve the properties of polylactic acid.

However, since the use of biodegradable polymers has expanded recently, requirements therefor have also increased, and the characteristics thereof have to be improved so as to be equivalent to those of general-purpose polymers. In order to respond to these requirements, attempts at blending existing general-purpose high polymers with biodegradable polymers have been made. As a result, although biodegradability cannot be expected, the use of biodegradable polymers has made it possible mainly to reduce the used amount of general-purpose resins derived from petroleum. Thus, there is the advantage that carbonic acid gas generation and combustion heat upon disposal are lowered. Therefore, this method draws attention as a method that can reduce environmental load. For example, Patent Document 3 discloses the method of blending polylactic acid with rubber-blended shock-resistant polystyrene as a means for improving the shock resistance of polylactic acid. However, since the method described in Patent Document 3 is a method in which polylactic acid and highly shock resistant styrene are melted and mixed, and the obtained resin composition has not reached compatibilization, the improvement in toughness and heat resistance is limited.

Patent Document 1: Japanese Patent Appl. Publ. No. 2000-219803
Patent Document 2: Japanese Patent Appl. Publ. No. 9-272794
Patent Document 3: Japanese Patent Appl. Publ. No. 2005-264086

DISCLOSURE OF THE INVENTION

Problems to be Solved by the Invention

Like in the example described above, most of the existing general-purpose polymers and biodegradable polymers are not compatible with each other. Therefore, it cannot be said yet that improving the properties of biodegradable polymers by blending them with general-purpose polymers is easy.

Therefore, a problem to be solved by the present invention is to provide a triblock copolymer that has a novel structure and is useful as a compatibilizing agent (dispersion aid) or the like in the polymer blending of an existing general-purpose polymer with a biodegradable polymer, particularly, polylactic acid or polycaprolactone.

Means for Solving the Problems

The inventors of the present invention have found that a triblock copolymer with a high molecular weight is generated when, after oligoolefin containing vinylidene bonds at both ends and is obtained by highly controlled thermal decomposition has been hydroxylated, a cyclic ester, such as a lactide, is subjected to ring-opening polymerization under the presence of oligoolefin containing hydroxyl groups at both ends. The inventors thus accomplished the present invention. More specifically, the present invention relates to (1) to (7) below.

(1) A triblock copolymer represented by the following general formula (i)

[Chemical Formula 1]

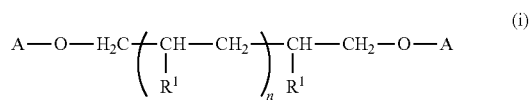

wherein each $R^1$ is independently selected from the group consisting of H, $-CH_3$, $-C_2H_5$, and $-CH_2CH(CH_3)_2$; n is an integer of 10 to 1000; and A represents a polyester block obtained by subjecting one or more cyclic esters selected from the group consisting of lactides, glycolides and lactones, to ring-opening polymerization.

(2) The triblock copolymer according to (1), wherein A is represented by the following general formula (ii)

[Chemical Formula 2]

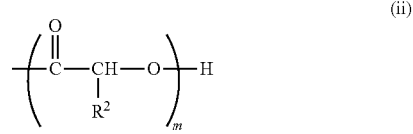

wherein $R^2$ represents a methyl group or hydrogen, and m is an integer of 1 to 1000.

(3) The triblock copolymer according to (1), wherein A is represented by the following general formula (iii)

[Chemical Formula 3]

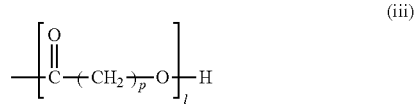

(iii)

wherein l represents an integer of 1 to 1000, and p represents an integer of 2 to 15.

(4) A method of producing a triblock copolymer, characterized in that one or more cyclic esters selected from the group consisting of lactides, glycolides and lactones, are subjected to ring-opening polymerization under the presence of oligoolefin containing hydroxyl groups at both ends represented by the following general formula (iv)

[Chemical Formula 4]

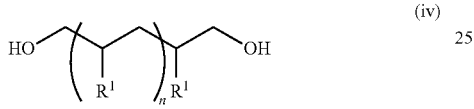

(iv)

In this formula, each $R^1$ is independently selected from the group consisting of H, —$CH_3$, —$C_2H_5$, and —$CH_2CH(CH_3)_2$, and n represents an integer of 10 to 1000.

(5) The production method according to (4), wherein the ring-opening polymerization is carried out with a metal derivative as catalyst.

(6) The production method according to (4), wherein a lactone having a 4 to 17 membered ring is subjected to the ring-opening polymerization with hydrolase as catalyst.

(7) The production method according to any of (4) to (6), comprising, as a step of obtaining the oligoolefin containing hydroxyl groups at both ends, a step of melting one or more polyolefins selected from the group consisting of polypropylenes, poly-1-butenes, ethylene/propylene copolymers, ethylene/1-butene copolymers, propylene/1-butene copolymers, and poly-4-methyl-1-pentenes, thermally decomposing the melt under reduced pressure while subjecting the melt to bubbling with an inert gas, and subsequently hydroxylating the product of the thermal decomposition.

Effects of the Invention

The triblock copolymer according to the present invention has blocks at both terminals derived from biodegradable polymers, and a block connecting them is composed of a general-purpose polymer. Therefore, the triblock copolymer can be utilized as a compatibilizing agent (dispersion aid) or the like in the blending of existing general-purpose resins and biodegradable polymers.

BEST MODES FOR CARRYING OUT THE INVENTION

Triblock Copolymer

Figure 1:
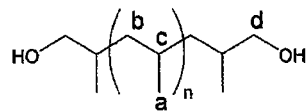
FIG. 1 is a proton NMR chart ($CDCl_3$) of the oligopropylene containing hydroxyl groups at both ends (iPP-OH) obtained in the reference example.
Figure 1:
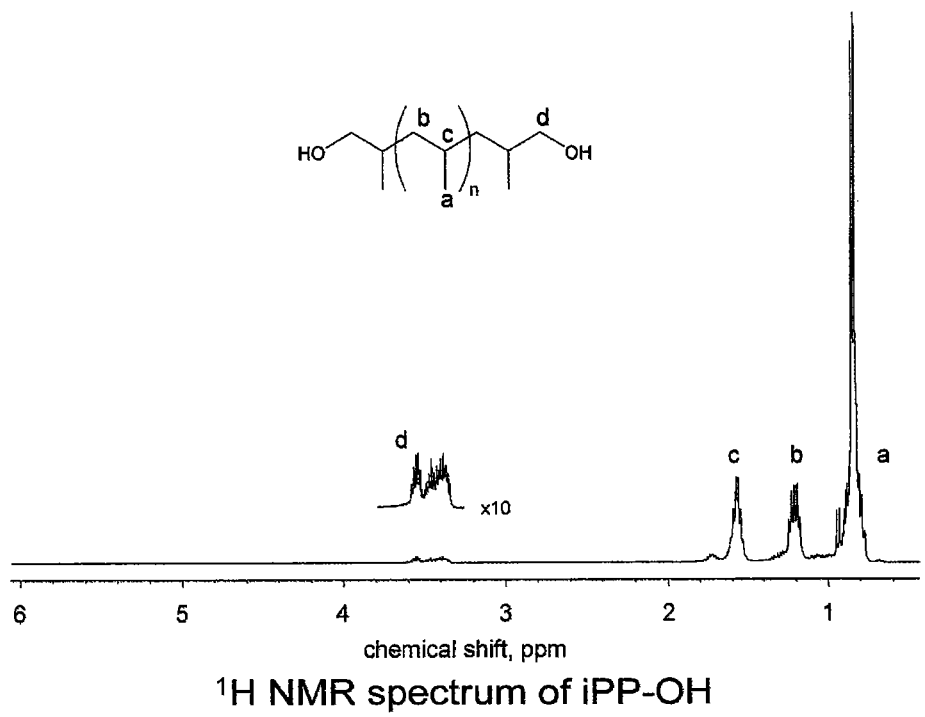

A triblock copolymer of the present invention is represented by the following general formula (i) and has a novel structure composed of polyester blocks at both ends derived from biodegradable polymers and a general-purpose polymer block connecting them.

[Chemical Formula 5]

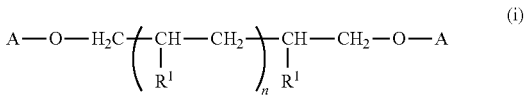

(i)

In the general formula (i), no particular limitation is imposed on the repetition unit number n. However, this number is normally an integer of 10 to 1000.

Each $R^1$ is independently selected from the group consisting of H, —$CH_3$, —$C_2H_5$, and —$CH_2CH(CH_3)_2$. More specifically, this includes cases in which the oligoolefin constituting an oligoolefin chain is, e.g., oligopropylene (all $R^1$ are —$CH_3$), oligo 1-butene (all $R^1$ are —$C_2H_5$), an ethylene/propylene copolymer ($R^1$ is H or —$CH_3$), an ethylene/1-butene copolymer ($R^1$ is H or —$C_2H_5$), a propylene/1-butene copolymer ($R^1$ is —$CH_3$ or —$C_2H_5$), or oligo 4-methyl-1-pentene (all $R^1$ are —$CH_2CH(CH_3)_2$). Note that the copolymers such as ethylene/propylene copolymer, include both random copolymers and block copolymers.

Meanwhile, A represents a polyester block obtained by ring-opening polymerization of one or more cyclic esters selected from the group consisting of lactides, glycolides, and lactones. Note that, in the present description, "lactides" include D-lactide, L-lactide, meso-lactide, and racemic lactide. Furthermore, "lactones" include lactones having various numbers of ring members (normally, 4 to 17) and also include those in which hydrogen bonded with carbon that constitutes a ring is substituted with, for example, an alkyl group, an alkenyl group, halogen, or a haloalkyl group. No particular limitation is imposed on the repetition unit number of the polyester blocks. However, this number is normally an integer of 1 to 1000.

Method of Producing Triblock Copolymer

The triblock copolymer of the present invention can be obtained by subjecting one or more cyclic esters selected from the group consisting of lactides, glycolides, and lactones to ring-opening polymerization under the presence of an oligoolefin containing hydroxyl groups at both ends represented by the following general formula (iv)

[Chemical Formula 6]

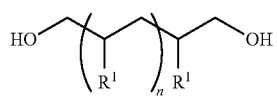

(iv)

In this formula, each $R^1$ is independently selected from the group consisting of H, —$CH_3$, —$C_2H_5$, and —$CH_2CH(CH_3)_2$, and n represents an integer of 10 to 1000.

The oligoolefin containing hydroxyl groups at both ends that serves as a raw material can be obtained by hydroxylating an oligoolefin containing vinylidene bonds at both ends.

The oligoolefin containing vinylidene bonds at both ends can be obtained as a product of thermal decomposition of polyolefin by highly controlled thermal decomposition (see Macromolecules, 28, 7973 (1995)) developed by the inventors of the present invention.

In the following, polypropylene is taken as an example for explanation. The thermal decomposition product obtained by the method of a highly controlled thermal decomposition of polypropylene has the characteristics that its number average molecular weight Mn is about 1,000 to 50,000, its dispersion degree Mw/Mn is about 2, the average number of vinylidene groups per one molecule is in the range of 1.5 to 1.9, and the stereoregularity of the raw material polypropylene before decomposition is maintained. The weight average molecular weight of the raw material polypropylene before decomposition lies preferably within the range of 10,000 to 1,000,000, more preferably within the range of 200,000 to 800,000.

As thermal decomposition equipment, the equipment disclosed in the Journal of Polymer Science: Polymer Chemistry Edition, 21,703 (1983) can be used. Polypropylene is placed in a reaction chamber of the thermal decomposition equipment made of Pyrex® glass, the melted polymer phase is subjected to intensive bubbling with a nitrogen gas under reduced pressure, and thermal decomposition reactions are carried out at a predetermined temperature for a predetermined period of time while volatile products are extracted from the melted polymer phase so that second-order reactions are suppressed. After the thermal decomposition reactions are finished, the residue in the reaction chamber is dissolved in hot xylene, subjected to hot filtration, and then purified by being subjected to reprecipitation by alcohol. The reprecipitated matter is filtrated and collected and subjected to vacuum drying, thereby obtaining oligopropylene containing vinylidene bonds at both ends.

The conditions of the thermal decomposition are adjusted in consideration of the results of an experiment carried out in advance, wherein the molecular weight of the product is predicted from the molecular weight of polypropylene before decomposition and the primary structure of the ultimately desired block copolymer. The thermal decomposition temperature is preferably in the range of 300° C. to 450° C. At temperatures lower than 300° C., the thermal decomposition reactions of polypropylene may not progress sufficiently. At temperatures higher than 450° C., the thermal decomposition product may deteriorate.

The hydroxylation can be achieved by hydroxylating the double bond of the oligoolefin containing vinylidene bonds at both ends, which is obtained in accordance with the above described method, by an oxidation reaction subsequent to hydroboration. For example, tetrahydrofuran is used as a solvent and, first, a boronation reagent is added so as to carry out hydroboration. As the boronation reagent, 9-borane bicyclononane or a borane-tetrahydrofuran complex can be used. When hydrogen peroxide water is added to the reaction solution after the hydroboration so as to cause oxidation reactions, oligoolefin containing hydroxyl groups at both ends is obtained.

Next, under the presence of the oligoolefin containing hydroxyl groups at both ends obtained in the above-described manner, one or more cyclic esters selected from the group consisting of lactides, glycolides, and lactones are subjected to ring-opening polymerization.

The ring-opening polymerization is roughly classified into methods that use a metal derivative as catalyst and methods that use hydrolase as catalyst.

Methods that use a metal derivative can be widely applied to ring-opening polymerization of cyclic esters such as lactides, glycolides, and lactones (see Macromolecules 2000, 33, 7395-7403 and Macromolecules 1999, 32, 4794-4801, etc.)

Examples of metal derivatives used as catalyst include metal derivatives of, for example, tin, zinc, lead, titanium, bismuth, zirconium, germanium, antimony, and aluminum. Because of its reactivity and the fact that the amount of generated impurities is small, trialkylaluminum is preferred, and triethylaluminum is even more preferably used.

Methods that use hydrolase as catalyst are suitable for the ring-opening polymerization that uses lactones with a comparatively large number of ring members (typically, lactones with 6 or more ring members) (see Network Polymer Vol. 23, No. 2 (2002), etc.)

Enzymes that hydrolyze the ester bond are used as the hydrolase without particular limitation. Herein, a lipase is preferred because of its availability and the thermal stability of the enzyme. CA lipase (*Candida antarctica* lipase), PPL (porcine pancreatic lipase), *Candida cylindraces* lipase, *Burkholderia cepacia* Lipase, Lipase PS, Lipozyme IM, etc. can be used without limitation. Among them, CA lipase is preferred. The enzyme may be immobilized or not. Examples of the lipase include Novozym 435 (product name) of Novo Nordisk Bio Industry A/S, which is an immobilized enzyme derived from *Candida antarctica*.

As a reaction solvent, solvents such as acetonitrile, 1,4-dioxane, tetrahydrofuran, isopropyl ether, toluene, and benzene that dissolve lactone polymers and do not deactivate enzymes can be used without limitation.

The polymerization temperature can be 30 to 85° C. In particular, the polymerization is preferably carried out at a temperature in the range of 40 to 75° C. When the temperature is lower than 30° C., the reaction speed is lowered. When the temperature exceeds 85° C., enzymes may be deactivated.

EXAMPLES

Hereinafter, the present invention will be explained in more detail by examples. However, the present invention is not limited to these examples. In the examples, the molecular weight was measured using GPC analysis equipment (HLC-8121 GPC/HT (produced by Tosoh Corporation)). In the measurement, THF was measured as the mobile phase, and the molecular weight in terms of polystyrene was determined. FT-NMR: JNM-GX400 (produced by JEOL Ltd.) was used as NMR. S-3000N produced by Hitachi was used as scanning-type electron microscope (SEM), and the observation was carried out at an acceleration voltage of 15 kV.

Reference Example

Synthesis of Oligopropylene Containing Hydroxyl Groups at Both Ends (iPP-OH)

Equipment for laboratory-scale highly controlled thermal decomposition with a maximum sample amount of 5 kg was used as thermal decomposition equipment. 2 kg of commercially available isotactic polypropylene (Novatec PP (Produced by Japan Polypropylene Corporation), grade: EA9A, melt flow index (MFR): 0.5 g/10 min) was put into a reactor, and after the system was subjected to nitrogen substitution, the pressure therein was reduced to 2 mmHg and the reactor was heated to 200° C., thereby melting the content. Then, the reactor was immersed in a metal bath set to 390° C., thereby carrying out thermal decomposition. During the thermal decomposition, the system was maintained in a pressure-reduced state at about 2 mmHg, and the melted polymer was agitated by bubbling of a nitrogen gas discharged from capillaries introduced into it. After 3 hours had passed, the reactor was removed from the metal bath and cooled to room temperature. Then, the reaction system was returned to normal pressure, and the residue in the reactor was dissolved in hot xylene and then dripped into methanol so as to carry out reprecipitation and purification. The yield of the obtained polymer was 77%, its number average molecular weight (Mn) was 7500, its dispersion degree (Mw/Mn) was 1.78, and the average number (fTVD) of terminal double bonds per one molecule was 1.78.

20 g of oligopropylene containing vinylidene bonds at both ends (Mn: 1000, Mw/Mn: 1.1, fTVD: 1.80) obtained by highly controlled thermal decomposition and 200 ml of tetrahydrofuran (THF) were put into a reactor. After nitrogen substitution, 60 ml of a borane-tetrahydrofuran complex ($BH_3$-THF) THF solution (1M) was added, and the mixture was heated for 3 hours under reflux. Then, in an ice bath, 60 ml of 5N sodium hydroxide solution was added, 60 ml of 30% hydrogen peroxide aqueous solution was subsequently added, and the mixture was heated for 15 hours under reflux. After the reactions, the reaction mixture was poured to methanol and subjected to reprecipitation and purification, thereby obtaining oligopropylene containing hydroxyl groups at both ends (iPP-OH).

Example 1

Synthesis of Triblock Copolymer (PLA-iPP-PLA)

0.2 g of the above-described oligopropylene containing hydroxyl groups at both ends (Mn: 1000) was put into a Schlenk tube. After nitrogen substitution, 5 ml of toluene was added, heated, and dissolved. Then, 1 ml of triethylaluminum/hexane 1M solution was added. After the mixture was agitated for 10 minutes, 1.44 g of L-lactide was added, and the mixture was agitated at 100° C. for 3 hours. After the reactions, 1 ml of 1NHCl aqueous solution was added as a terminating agent, and reprecipitation and purification were carried out with 200 ml of methanol. The obtained copolymer was analyzed by using GPC. As a result, Mn was 4800, and Mw/Mn was 1.17.

Example 2

Synthesis of Triblock Copolymer (PCL-iPP-PCL)

0.2 g of the above-described oligopropylene containing hydroxyl groups at both ends (Mn: 1000) and 0.1 g of Novozyme 435 (Lipase) were put into a Schlenk tube. After nitrogen substitution, 4 ml of toluene was added, heated, and dissolved. Then, 2 ml of s-caprolactone was added, and the mixture was agitated at 60° C. for 2 hours. After the reactions, Novozyme 435 was separated by filtration, and reprecipitation and purification were carried out with 200 ml of methanol. For the obtained copolymer, Mn was 11000 and Mw/Mn was 1.7.

Figure 2:
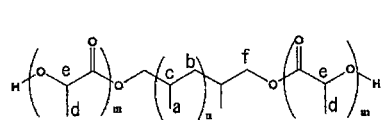
FIG. 2 is a proton NMR chart ($CDCl_3$) of the triblock copolymer (PLA-iPP-PLA) obtained in Example 1.
Figure 2:
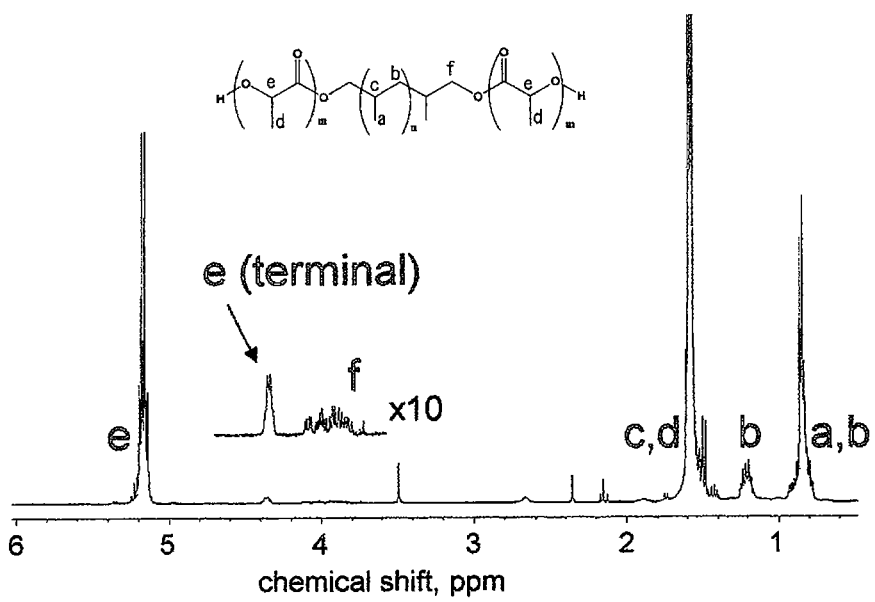
Figure 3:
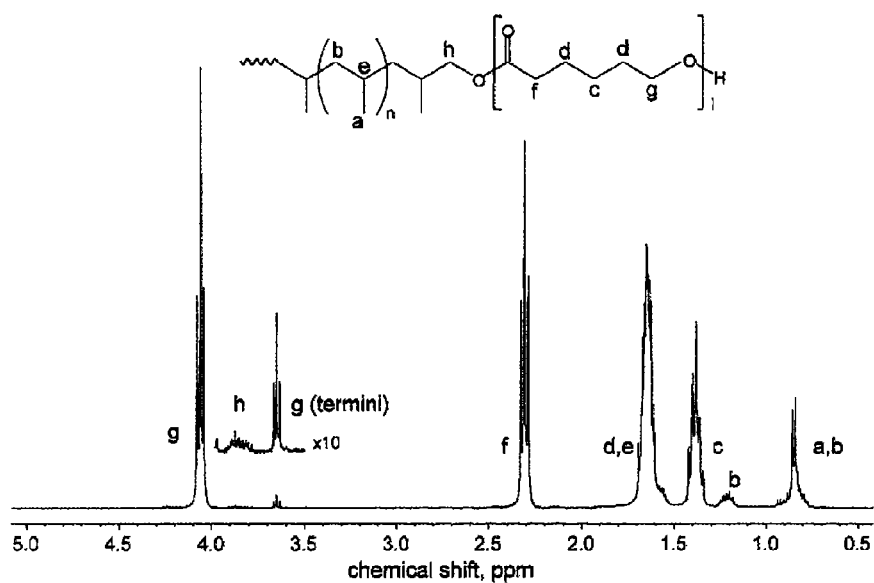
FIG. 3 is a proton NMR chart ($CDCl_3$) of the triblock copolymer (PCL-iPP-PCL) obtained in Example 2.

FIG. 1 shows a proton NMR chart of the oligopropylene containing hydroxyl groups at both ends (iPP-OH) obtained in the reference example. FIG. 2 shows a proton NMR chart of the triblock copolymer (PLA-iPP-PLA) obtained in Example 1. FIG. 3 shows a proton NMR chart of the triblock copolymer (PCL-iPP-PCL) obtained in Example 2.

In FIG. 2, the signals of protons derived from polylactic acid blocks are observed near 4.4 ppm (terminal) and 5.2 ppm. In FIG. 3, the signals of methylene protons derived from poly ε-caprolactone blocks are observed near 3.6 ppm (terminal) and 4.1 ppm.

Since the acyl shift of terminal methylene protons of iPP-OH has been confirmed in FIG. 2 and FIG. 3, it can be understood that the hydroxyl group of iPP-OH reacted with lactide or ε-caprolactone, and a triblock copolymer was generated.

Example 3

Figure 4:
FIG. 4 is an SEM image obtained in Example 3.

Evaluation of Compatibilizing Performance of PCL-iPP-PCL 0.45 g of isotactic polypropylene (Novatec PP EA9, Mn: 160,000, produced by Japan Polypropylene Corporation), 0.45 g of polycaprolactone (produced by Aldrich, Mn: 80,000), and 0.1 g of PCL-iPP-PCL (Mn: 11000) were collected and subjected to heating and agitation at 140° C. in an eggplant flask together with 50 ml of xylene. After they were completely dissolved, the mixture was slowly dripped into 500 ml of methanol, and the generated precipitate was collected and then subjected to reduced-pressure heat drying, thereby obtaining a blended powder. The blended powder was subjected to heat pressing at 200° C., thereby generating a sheet. The obtained sheet was cooled with liquid nitrogen and ruptured, its PCL phase then was etched under chloroform reflux, and subsequently, the ruptured surface was observed by SEM (FIG. 4).

Comparative Example

Figure 5:
FIG. 5 is an SEM image obtained in the comparative example.

Compatibility Evaluation of iPP and PCL 0.5 g of isotactic polypropylene (iPP, Novatec PP EA9, Mn: 160,000, produced by Japan Polypropylene Corporation) and 0.5 g of polycaprolactone (PCL, produced by Aldrich, Mn: 80,000) were collected and subjected to heating and agitation at 140° C. in an eggplant flask together with 50 ml of xylene. After they were completely dissolved, the mixture was slowly dripped into 500 ml of methanol, and the generated precipitate was collected and then subjected to reduced-pressure heat drying, thereby obtaining a blended powder. The blended powder was subjected to heat pressing at 200° C., thereby generating a sheet. The obtained sheet was cooled with liquid nitrogen and ruptured, its PCL phase then was etched under chloroform reflux, and subsequently, the ruptured surface was observed by SEM (FIG. 5).

When the SEM image of Example 3 is compared with that of the comparative example, the size of holes derived from the PCL phase is obviously reduced in Example 3. Therefore, the compatibilization ability of PCL-iPP-PCL can be confirmed.

INDUSTRIAL APPLICABILITY

The triblock copolymer according to the present invention can be utilized as a compatibilizing agent (dispersion aid) or the like in the polymer blending of an existing general-purpose resin with polylactic acid or polycaprolactone.

With the method of producing a triblock copolymer according to the present invention, a polymer having a high molecular weight can be produced by using a polymer which is contained in waste, etc. as a starting material. Therefore, this method is extremely useful as a polymer recycling method as well.

The invention claimed is:

1. A method of producing a triblock copolymer, wherein one or more cyclic esters selected from the group consisting of lactides, glycolides and lactones are subjected to ring-opening polymerization under the presence of oligoolefin containing hydroxyl groups at both ends, represented by the following general formula (iv)

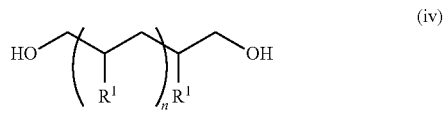

wherein each $R^1$ is independently selected from the group consisting of H, —$CH_3$, —$C_2H_5$, and —$CH_2CH(CH_3)_2$, and n represents an integer of 10 to 1000, the method comprising, as steps of obtaining the oligoolefin containing hydroxyl groups at both ends:
  melting one or more polyolefins selected from the group consisting of polypropylenes, poly-1-butenes, ethylene/propylene copolymers, ethylene/1-butene copolymers, propylene/1-butene copolymers, and poly-4-methyl-1-pentenes;
  thermally decomposing the melt under reduced pressure while subjecting the melt to bubbling with an inert gas; and
  subsequently hydroxylating the product of the thermal decomposition.

2. The production method according to claim 1, wherein the ring-opening polymerization is carried out with a metal derivative as catalyst.

3. The production method according to claim 1, wherein a lactone having a 4 to 17-membered ring is subjected to the ring-opening polymerization with a hydrolase as catalyst.

* * * * *